US006760617B2

(12) United States Patent
Ward et al.

(10) Patent No.: US 6,760,617 B2
(45) Date of Patent: Jul. 6, 2004

(54) METHOD AND DEVICE FOR MEASURING TISSUE OEDEMA

(75) Inventors: Leigh Ward, Kenmore Hills (AU); Bruce Herbert Cornish, Greenbank (AU)

(73) Assignees: The University of Queensland, Queensland (AU); Queensland University of Technology, Queensland (AU)

(*) Notice: Subject to any disclaimer, the term of this patent is extended or adjusted under 35 U.S.C. 154(b) by 188 days.

(21) Appl. No.: 10/029,015

(22) Filed: Dec. 20, 2001

(65) Prior Publication Data

US 2002/0161311 A1 Oct. 31, 2002

Related U.S. Application Data

(63) Continuation of application No. PCT/AU00/00702, filed on Jun. 22, 2000.

(51) Int. Cl.[7] .................................................. A61B 5/05
(52) U.S. Cl. ........................................................ 600/547
(58) Field of Search ................................ 600/372, 382, 600/384, 393, 547, 548

(56) References Cited

U.S. PATENT DOCUMENTS 6,151,523 A * 11/2000 Rosell Ferrer et al. ..... 600/547

OTHER PUBLICATIONS

Bracco, D. et al., 1998, Critical Care Medicine, vol. 26 No. 6, pp. 1065–1070.
Chiolero, R.L., et al., 1992, Intensive Care Medicine, vol. 18, pp. 322–326.
Chumlea, et al., 1994, Nutrition Reviews, vol. 52, No. 4, pp. 123–131.
Cornish, B.H., et al., 1996, Breast Cancer Research and Treatment, vol. 38, pp. 169–176.
Cornish, B.H., et al., 1998, Applied Radiation and Isotopes, vol. 49 No. 5/6, pp. 651–652.
De Luca, F., et al., 1996, Physics in Medicine and Biology, vol. 41, pp. 1863–1869.
Derwent Abstract No. 97–474414, JP 09 220209 A (Sekisui Chem Ind Co Ltd) Aug. 26, 1997, see abstract.
Derwent Abstract No. 99–138541, JP 10 014898 A (Sekisui Chem Ind Co Ltd) Jan. 20, 1998, see abstract.
Derwent Abstract No. 99–138542, JP 10 014899 A (Sekisui Chem Ind Co Ltd) Feb. 20, 1998, see abstract.
Derwent Abstract No. 99–247542, JP 11 070090 A (Sekisui Chem Ind Co Ltd) Mar. 16, 1999. see abstract.
Duerenberg, P., et al., 1996, Annals of Human Biology, vol. 23, No. 1, pp 31–40.
Kim, C.T., et al., 1997, Electromyography and Clinical Neurophysiology, vol. 37, pp. 297–304.
Rigaud, B. et al., 1996, Critical Reviews in Biomedical Engineering, vol. 24 (4–6), pp. 257–351.
Steijaert, M., et al., 1997, International Journal of Obesity, vol. 21, pp. 930–934.
Thomas, B.J., et al., 1998, Applied Radiation and Isotopes, vol. 49 No. 5/6, pp. 447–455.
Ward, L.C., et al., 1992, European Journal of Clinical Investigation, vol. 22, pp. 751–754.

* cited by examiner

Primary Examiner—Max F. Hindenburg
Assistant Examiner—Jonathan Foreman
(74) Attorney, Agent, or Firm—Morgan, Lewis & Bockius, LLP

(57) ABSTRACT

The present invention provides a method of assessing tissue oedema, in particular lymphoedema, by measuring bioelectrical impedance at a single frequency. Comparison of a single frequency bioelectrical impedance measurement taken at an anatomical region affected by tissue oedema to that taken at an anatomical region unaffected by tissue oedema is a reliable indicator of the presence or possible presence of lymphoedema. The present invention further provides an apparatus for determining the presence of tissue oedema.

32 Claims, 6 Drawing Sheets

METHOD AND DEVICE FOR MEASURING TISSUE OEDEMA

CROSS-REFERENCE TO RELATED APPLICATIONS

This application is a continuation of International Patent Application No. PCT/AU00/00702, filed Jun. 22, 2000, which claims priority to Australian Application No. PQ1137, filed Jun. 22, 1999.

FIELD OF THE INVENTION

This invention relates to the measurement of tissue oedema and, in particular, lymphoedema using bioelectrical impedance analysis.

BACKGROUND

Measurement of extracellular tissue fluid may be of importance in a range of situations. This is particularly so in the case of lymphoedema which is a condition characterised by excess protein and oedema in the tissues as a result of reduced lymphatic transport capacity and/or reduced tissue proteolytic capacity in the presence of a normal lymphatic load. Lymphoedema normally occurs in a limb and may cause pain, scarring and reduced limb function. The condition is incurable, progressive, often disfiguring and physically disabling. Its course, however, can be arrested or slowed by intervention using physical therapy, compression bandaging, massage and other physical techniques.

Acquired or secondary lymphoedema is caused by damaged or blocked lymphatic vessels. The commonest inciting events are surgery and/or radiotherapy. However, onset of lymphoedema is unpredictable and may develop within days of its cause or at any time during a period of many years after that cause.

There is a need for an accurate and effective technique to detect the onset of lymphoedema, assess its severity and monitor its response to treatment. The simplest known technique involves measurement of limb circumferences and comparison with a paired unaffected limb. A further technique is available by way of immersion of the affected part and measurement of displaced liquid with subsequent comparison against the result of the same measurement performed on an unaffected limb.

It is also known to use multiple frequency bioelectrical impedance analysis (MFBIA) to assess lymphoedema (Watanabe et al., 1989, Lymphology 22:85). The authors noted that when a low frequency voltage is applied to tissue, the impedance of the cell membrane is substantial. With increased frequency, the impedance of the cell membrane decreases and current is able to flow through both extracellular and intracellular fluids. The results obtained by Watanabe et al were subject to analysis of equivalent resistivity of extracellular and intracellular fluid calculated after measurement of electrical bioimpedance at multiple frequencies. Further development of the technique was subsequently disclosed (Ward et al., 1992, European Journal of Clinical Investigation 22:751) in which MFBIA was used and the impedance at zero frequency was estimated by extrapolation. Differences were then calculated between left-hand and right-hand sides of patients for the impedance calculations 50 kHz and 0 kHz frequency. The bilateral differences in impedance between a group of controls and a group of affected patients were significant. This test relies on the use of a multifrequency bioimpedance meter and relatively complex analysis of the results to provide an indication of lymphoedema.

U.S. Pat. No 5,372,141 describes a body composition analyser that provides information in relation to body fat and ideal body weight. The analyser compares the bioimpedance of the body "network" against a reference network of known impedance. It is, however, of little or no use in assessing tissue oedema.

U.S. Pat. No 4,947,862 discloses an analyser to determine the amount of body fat on a patient. The analyser uses a high frequency low-voltage signal in the body and measures magnitudes and phase shift of the induced signal but again is of little use in measuring tissue oedema.

It would be of advantage to provide a method for determining the presence of oedema and, in particular, lymphoedema by measurements taken at a single frequency. It would further be advantageous to produce a device for measuring bioelectrical impedance at a single frequency and analysing that measurement to produce an indicator of the presence of oedema.

OBJECT OF THE INVENTION

It is an object of the present invention to overcome or ameliorate one or more of the difficulties of known methods used to assess tissue oedema and, in particular, lymphoedema.

DISCLOSURE OF THE INVENTION

In one form, although it need not be the only or broadest form, the invention resides in a method of assessing tissue oedema comprising the steps of:

performing a first measurement of bioelectrical impedance of a first anatomical region in a subject at a single low frequency alternating current;

performing a second measurement of bioelectrical impedance of a second anatomical region in the same subject at the same low frequency alternating current; and analysing the two measurements to obtain an indication of the presence of tissue oedema.

The first anatomical region and second anatomical region may be paired with at least one of the anatomical regions unaffected by tissue oedema.

Alternatively, the first and second anatomical regions may be dissimilar with at least one of the anatomical regions unaffected by tissue oedema.

The first anatomical region and the second anatomical region may be the same region with the first and second measurements separated in time. The anatomical regions may be limbs or parts of limbs.

The low frequency is preferably in the range of 5 to 20 kHz. More suitably, the range is 10 to 15 kHz. Most preferably, the measurements are made at 10 kHz.

The analysis may include the step of dividing the lesser result of the two measurements into the greater result of the two measurements to obtain a product or quotient. The results of the two measurements may further include the steps of applying a correcting factor or term to the product and deriving an indication of tissue oedema.

The step of analysing the two measurements may be conducted according to the algorithm $$F = \frac{Z_h}{Z_l} - cf$$

where:

F is an indication of the presence of tissue oedema;

$Z_h$ is the greater bioelectrical measurement;

$Z_l$ is the lesser bioelectrical measurement; and cf is a correcting factor.

The method may include the step of establishing "cf". Establishing "cf" may include the step of establishing a ratio of the bioelectrical impedance of a first anatomical region of at least one subject unaffected by tissue oedema compared to the bioelectrical impedance of a second anatomical region of that subject wherein the first and second anatomical regions of the at least one unaffected subject are paired with the first and second anatomical regions of the subject being assessed for tissue oedema.

When analysing the results of two measurements obtained on paired limbs, the correcting factor may suitably be 1.066.

Alternatively, the step of analysing the two measurements may be conducted according to the algorithm $$F = cf_1 - \frac{Z_l}{Z_h}$$

where:

F is an indication of the presence of tissue oedema;

$cf_1$ = a correcting factor;

$Z_l$ is the lesser bioelectrical impedance measurement; and $Z_h$ is the greater bioelectrical impedance measurement.

When analysing the results of two paired limbs $cf_1$ may be 0.862.

The indication of tissue oedema may be displayed by the step of representing the indication as a position on a scale.

In an alternate form, the invention resides in an apparatus for determining the presence of tissue oedema, including:

current means for applying an alternating current to an anatomical region at a single frequency;

monitoring means to monitor the bioelectrical impedance of said region and produce signals characteristic of bioimpedance; and analysis means to analyse the signals indicative of bioimpedance to provide an indication of tissue oedema.

The current means may suitably be a proximal electrode and distal electrode in electrical connection with a power source. The monitoring means is suitably a first connection and second connection for location on or near the anatomical region. Preferably, the monitoring means includes display means to display the signals indicative of bioimpedance.

Suitably; the analysis means is at least one processing means programmed to perform analysis of data to provide an indication of the presence of tissue oedema.

The analysis means may be programmed to analyse data according to the algorithm $$F = \frac{Z_h}{Z_l} - cf$$

where:

F is an indication of the presence of tissue oedema;

$Z_h$ is a greater bioelectrical impedance measurement obtained from a first anatomical region;

$Z_l$ is a lower bioelectrical impedance measurement obtained from a second anatomical region; and cf is a correcting factor.

Suitably, cf may equal 1.066 when the first and second anatomical regions of a subject undergoing assessment for tissue oedema are paired limbs.

The apparatus preferably includes means for recording bioimpedance in anatomical regions of the same subject simultaneously.

Preferably, said means includes duplicated electrodes and connections.

DETAILED DESCRIPTION OF THE DRAWINGS

Figure 1:
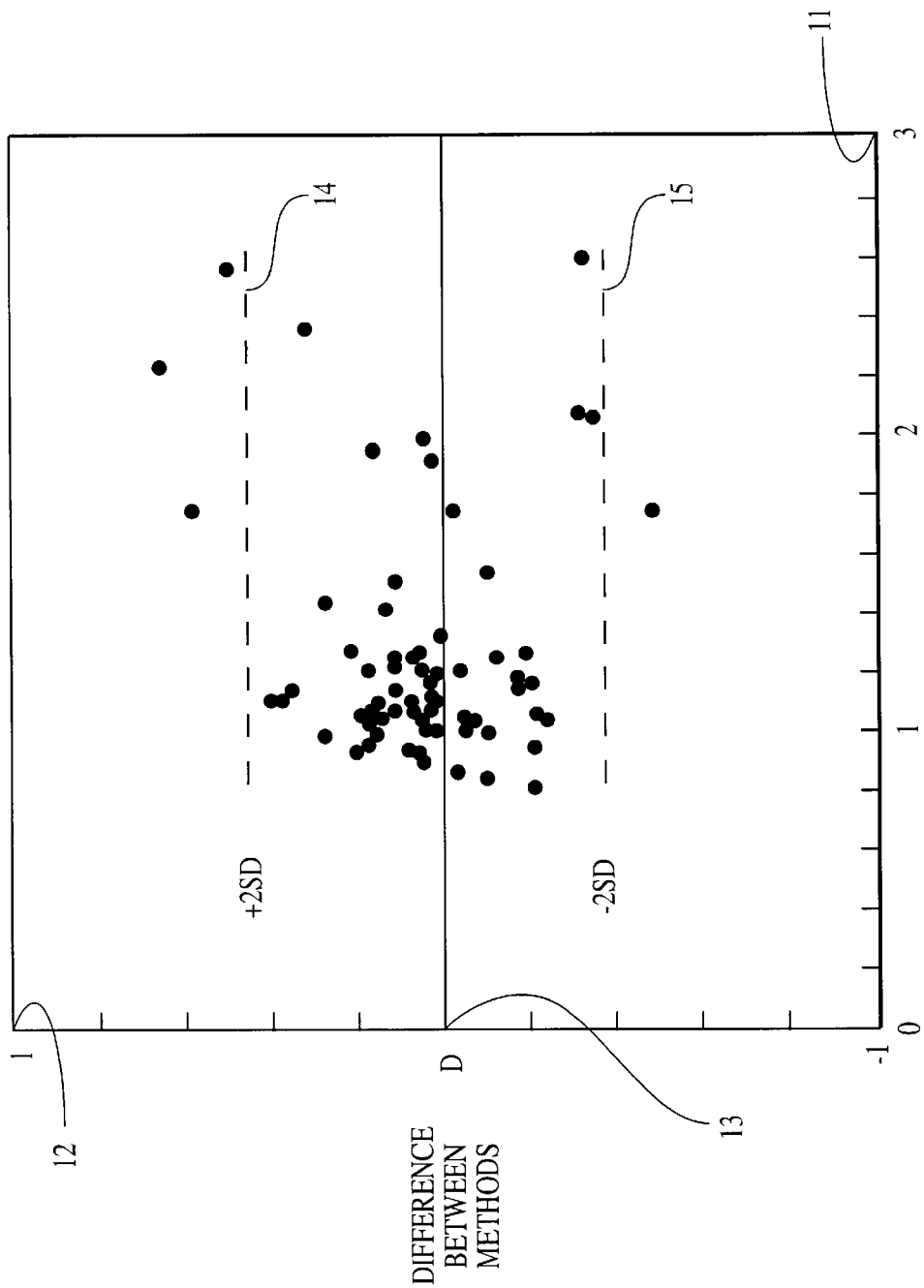
FIG. 1 represents the results of Limits of Agreement Analysis between MFBIA analysis and the method of the invention.

In the following discussion, like numbers apply to like parts.

The inventors have discovered a method of assessing tissue oedema based on measuring bioelectrical impedance at a single low alternating voltage frequency and, hence, alternating current frequency. "Low" in this specification means up to 30 kHz. In order to interpret readings taken at the single frequency, it is necessary to compare a reading taken at an anatomical region of interest against a second reading.

The second reading may be taken in a paired unaffected anatomical region. For example, a first measurement may be made at a location on the left leg and a second measurement made at the same location on the right leg of the same patient where the right leg is unaffected by tissue oedema. It is clear to a skilled addressee that other paired anatomical regions may be similarly used when performing the invention. For example, paired areas of the thorax may be assessed.

It is, however, possible to take the second reading at a dissimilar anatomical region. For example, the first reading may be taken on a leg and a second reading may be taken on an arm. The analysis of these readings will necessarily involve some different considerations, such as a different correcting factor. Again, it is clear to a skilled addressee that a wide range of dissimilar anatomical structures may be used for these measurements, such as a leg and the chest wall. This form of the method is of particular use where two paired anatomical sites are both affected by tissue oedema. The comparison of readings taken in two such affected sites will be distorted and will not produce a reliable indicator of tissue oedema.

As a further alternative, the method of the invention may be applied to two or more readings on the same anatomical region of a subject where those readings are separated in time. For example, a series of readings may be taken on a single limb subsequent to surgery with a known risk of lymphoedema as a side effect. Analysis of any two or more readings may indicate the early stage of developing lymphoedema and thereby provide a distinct advantage in that the prognosis may be greatly improved by early and aggressive therapeutic intervention. This technique may also be used to monitor the progress of lymphoedema with comparison made between measurements of an affected site.

The single frequency is suitably in a range such as 5 to 20 kHz as at this level, the impedance of cell walls is high and current flows mainly through extracellular fluid. Information obtained from readings at a low frequency therefore relates essentially to the extracellular fluid. The preferred range is in the order of 10 to 15 kHz and preferably measurements are made at 10 kHz.

Comparison of the results of measuring the bioelectrical impedance may be compared by dividing a lesser result into a greater result to provide a product greater than 1. For example, when comparing bioimpedance readings in paired limbs of unaffected subjects, there is typically a variation between sides due to the effect of left- or right-handedness or dominance. The results of surveying a population have established that when the lesser measurement is divided into the greater, over 99% of the clinically unaffected population will have a result less than 1.066. This figure may be used as a correcting factor when comparing paired limbs.

With increasing tissue oedema, the bioimpedance reading will decrease, thereby resulting in a greater product as a smaller reading is divided into the relatively constant reading of an unaffected limb or other anatomical region. As the difference between the product and the correcting factor increase, the likelihood of tissue oedema being present also increases, as discussed further below.

In the case of comparison of any two dissimilar regions, a correcting factor may be established by surveying a population of clinically unaffected subjects.

The inventors have found that a comparison of impedance of two anatomical regions at a single low level frequency of current will produce a reliable indicator of the presence or possible presence of lymphoedema. This overcomes the need to use multifrequency bioelectrical impedance analysis. The present testing method is quicker and simpler and the apparatus is substantially cheaper to produce. In addition, the complex analysis of MFBIA is avoided.

As there is some overlap between the results of unaffected subjects and those affected by tissue oedema, the determination of its presence is more accurate when the disparity between the quotient and the correcting factor is large.

A suitable classification of results when comparing paired sites on limbs is as follows.

| RANGE | EXAMPLE | RESULT |
|---|---|---|
| <1.066 | 1.02 | – |
| 1.066–1.10 | 1.08 | + |
| 1.1–1.2 | 1.15 | ++ |
| >1.2 | 1.3 | +++ |

In the above results, the example is the actual result of analysing readings taken from a subject. The presence of lymphoedema of increasing severity is represented by increasing numbers of "+" signs.

The inventors' preferred method of analysis is to divide the lesser bioimpedance reading into the greater to thereby produce a quotient greater than 1 and to then subject that quotient to subtraction of a correcting factor.

However, it is clear to a skilled addressee that the higher reading could be divided into the lesser to provide a fractional ratio less than one. That ratio could then be subtracted from a correcting factor determined from an unaffected control group. The algorithm for this process could be:

$$F = cf_1 - \frac{Z_l}{Z_h}$$

$cf_1$ is a correcting factor which may be established by surveying subjects unaffected by lymphoedema and dividing a lower impedance reading of one region by a larger impedance reading for a paired region. It has been found that over 99% of the unaffected population will have a ratio of 0.862 or greater when comparing paired limbs on the same subject.

The inventors have arranged trials of the method of their invention on approximately 70 subjects in which contemporaneous assessment was made using the known MFBIA technique to assess tissue oedema. FIG. 1 is a graph of the results of limits of agreement of analysis between MFBIA analysis and the present method. The graph has an X axis 11 recording the mean of the methods and a Y axis 12 recording difference between the methods around a zero line 13. The limits of plus and minus two standard deviation variations are set by lines 14, 15, respectively. The mean agreement between the methods is very high with only a 3.6% difference. The majority of the results also fall well within the two standard deviation agreement limits which also indicates a high level of agreement between the methods.

Figure 2:
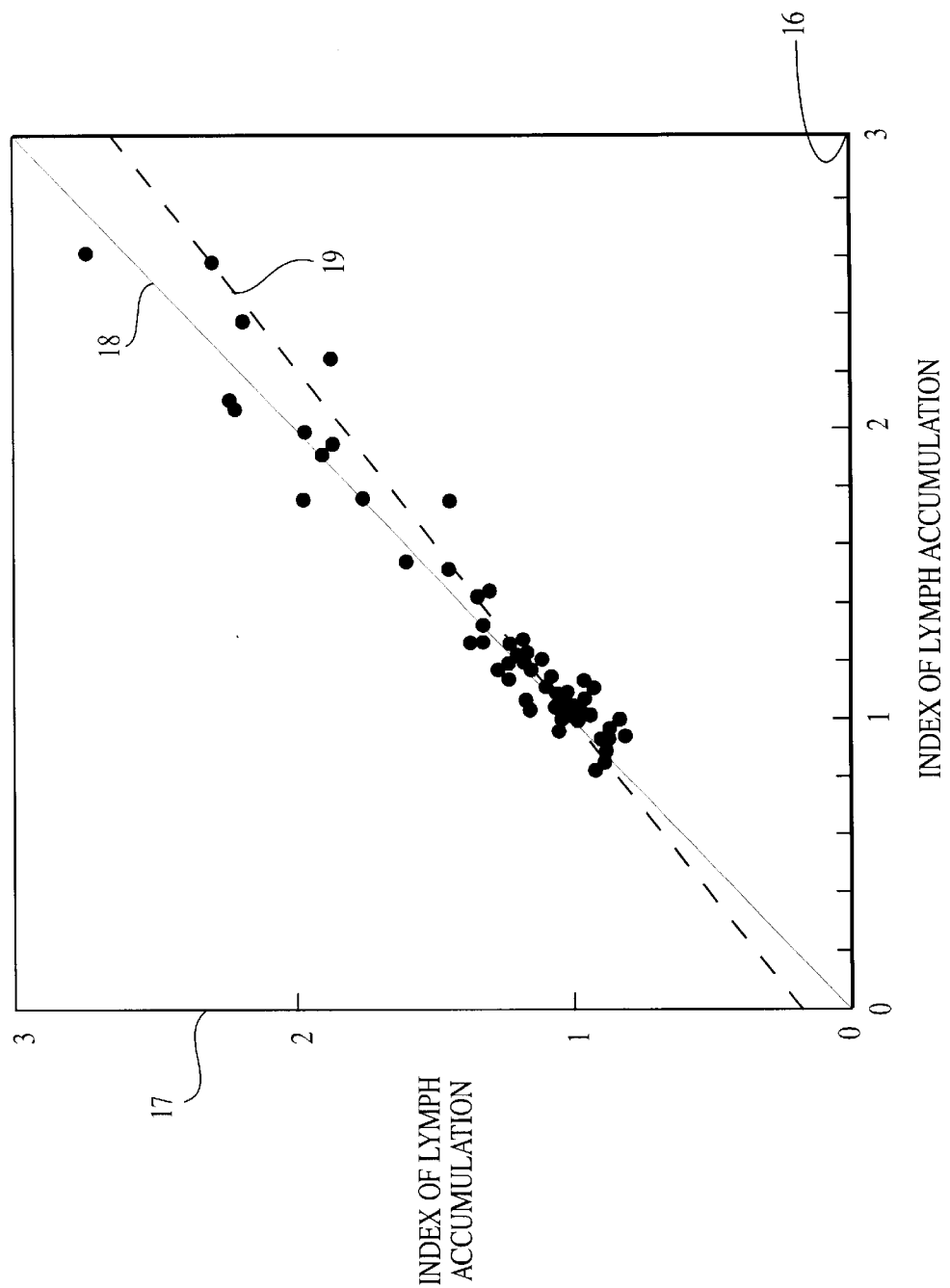
FIG. 2 represents the results of Correlation Analysis between MFBIA analysis and the method of the present invention.

Referring to FIG. 2, there is shown a graph representing the results of correlation analysis between MFBIA analysis and the method of the present invention. An index of lymph accumulation as measured by MFBIA analysis is shown on the X axis 16 and an index of lymph accumulation as measured by the present method is shown on the Y axis 17. A line of identity 18 is plotted, as is a line of best fit 19. The correlation between the methods is high at 0.87.

The result of these comparative methods is to establish that the present method works as well as an MFBIA approach but it is clearly much simpler, since it avoids the technical complexity required for MFBIA measurement and also the difficulty of an analysis which requires complex mathematical modelling.

Figure 3:
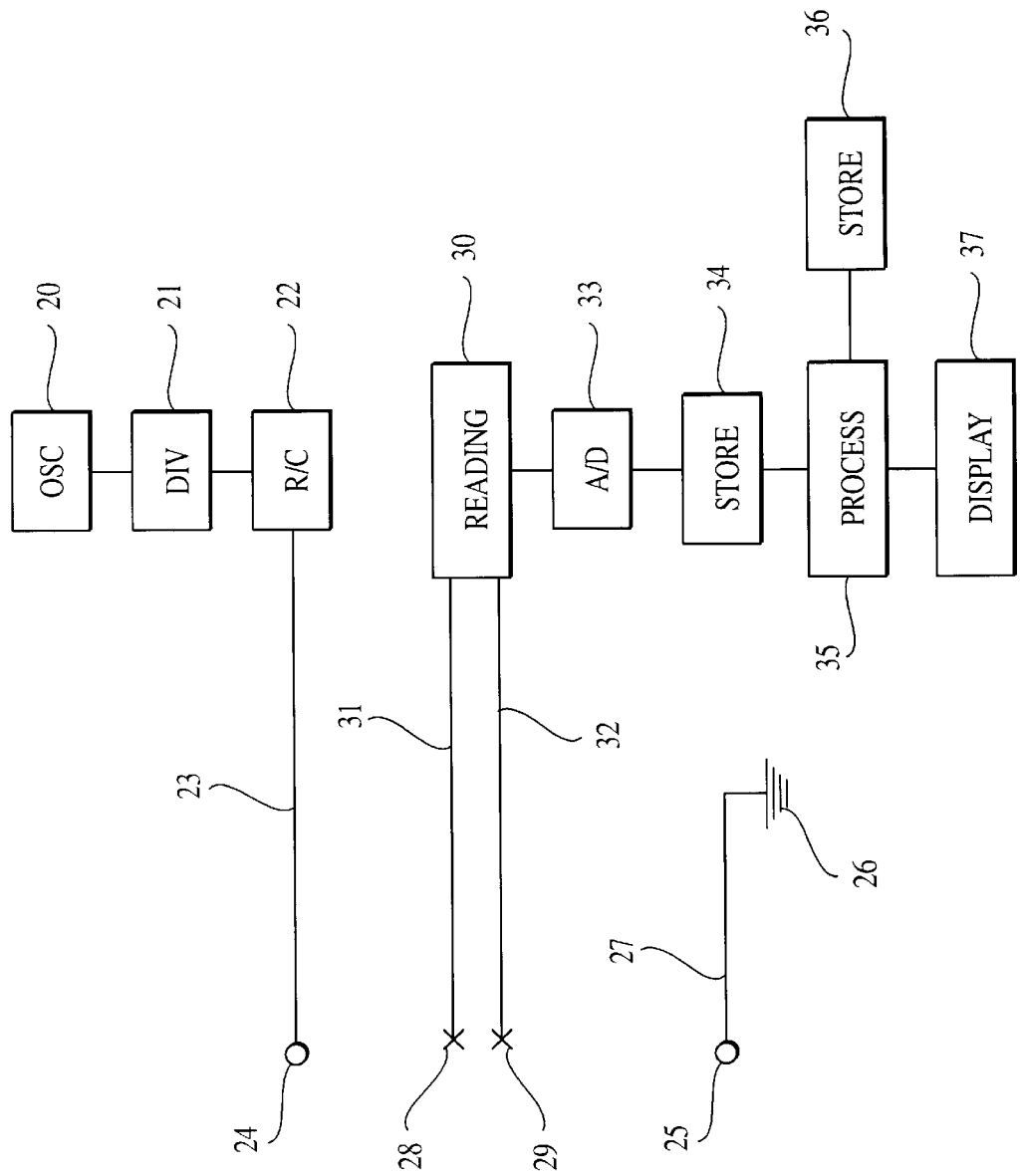
FIG. 3 is a schematic drawing of the apparatus of the invention.

Referring to FIG. 3, there is shown an apparatus for performing the method of the invention. It includes an oscillator 20, divider 21 and filter 22 connected in series to produce alternating current of a desired frequency when connected to a power source (not shown). The alternating current passes through cable 23 to electrode 24 through intervening tissue (not shown) to electrode 25 which is connected to earth 7 via cable 27. Monitoring electrodes 28, 29 are in connection with bioimpedance measuring meter 30 via cables 31, 32. Signals from bioimpedance measuring meter 30 are passed to analogue/digital convertor 33 which is in signal connection with data storing unit 34 which retains the digitised reading of bioimpedance.

A first reading of bioelectrical impedance is taken from a first anatomical region of a subject and stored in data storing unit 34.

A second reading is taken from a second anatomical region of the same subject. On receipt of the second reading, the processor 35 analyses the two readings according to the algorithm $$F = \frac{Z_h}{Z_l} - cf$$

where F is an indicator of the presence of tissue oedema, $Z_h$ is the greater impedance measurement, $Z_l$ is the lesser bioelectrical impedance measurement and cf is the correcting factor. The greater the difference between the product of $$\frac{Z_h}{Z_l}$$

and the correcting factor, the greater is the chance of the presence of tissue oedema.

The processor 35 transfers the result to second data storing unit 36, and the result is also presented on display 37. The display may be a scale with a movable indicator. It may also be a simple series of lights which, when illuminated, indicate any one of "unaffected", "possibly affected" or "affected". The display may be any other suitable form of indicator.

Figure 4:
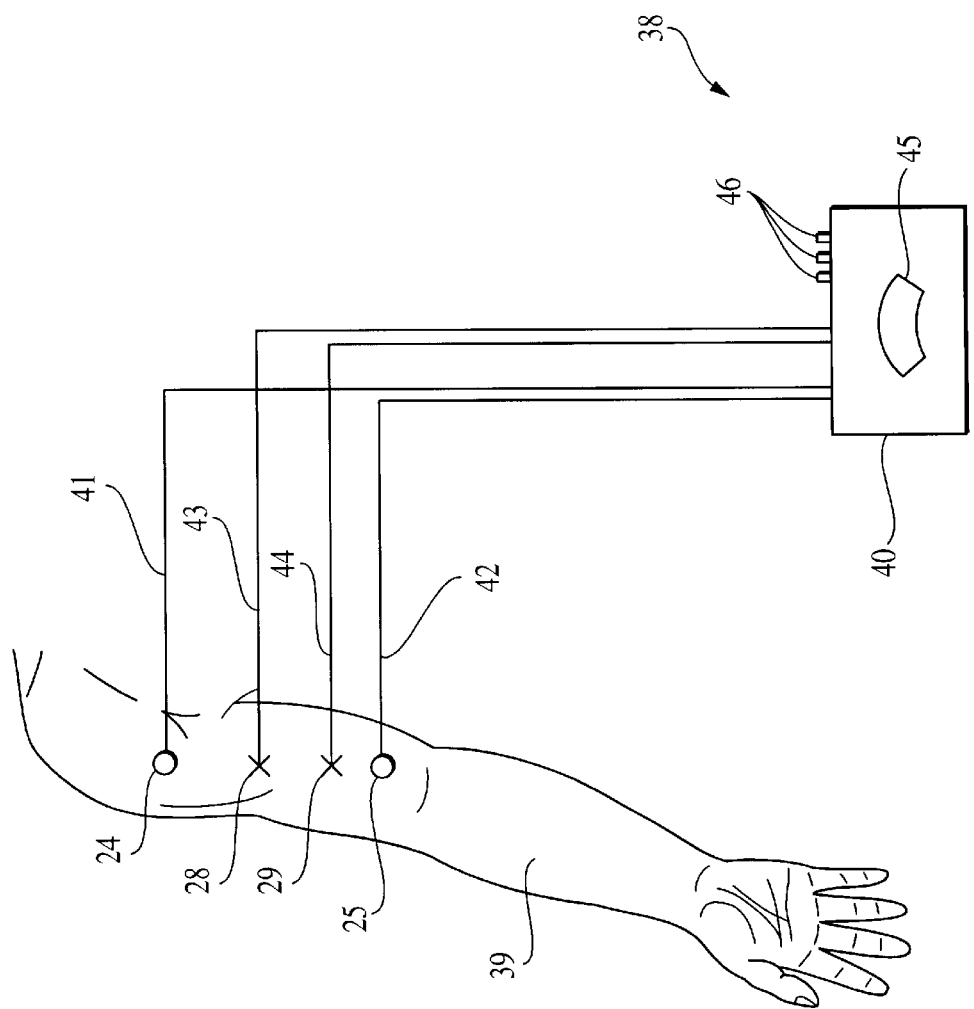
FIG. 4 is a diagram of the apparatus of the invention applied to the arm of a subject.

FIG. 4 shows an apparatus 38 of the invention attached to a subject's arm 39. Electrodes 24, 25 are applied at spaced positions on the subject's skin. A module 40 is in connection with the electrodes 24, 25 through electrical leads 41, 42. Module 40 includes the power source which provides alternating current between the electrodes 24, 25 at a set frequency. The inventors have found that the alternating current is preferably at a frequency between 5 to 20 kHz but, most preferably, at 10 kHz.

Monitoring electrodes 28, 29 are applied to the skin. They are separated from each other but located between electrodes 24, 25 and connected via electrical leads 43, 44 to a bioelectrical impedance measuring meter (not shown) in module 40.

A reading of bioelectrical impedance is taken on one limb and stored in first data storing unit (see FIG. 1).

The electrodes 24, 25 and monitoring electrodes 28, 29 may then be located in similar positions on the contra-lateral limb and a reading of bioelectrical impedance taken in a similar manner. A similar step may be conducted on dissimilar anatomical regions, such as an arm and a leg or on the same anatomical site at different times. For example, in the latter case, a regular reading may be taken every month to monitor changes in an anatomical region.

Module 40 further includes a processor programmed to divide the lesser of the bioelectrical impedance reading into the greater to produce a quotient. A correcting factor is then applied to the quotient to provide an indication of the presence of lymphoedema.

A correcting factor may be established by surveying a population of clinically unaffected subjects.

If a limb is affected by lymphoedema, its bioelectrical impedance will decrease due to the presence of extracellular fluid. Therefore, the variation between the impedance of the two limbs is such as to move the quotient of the two measurements outside the expected range for an unaffected population.

As shown in FIG. 4 the result may be displayed in display window 45 and by illumination of one of the three LEDs 46 which individually represent indications of "unaffected", "possibly affected" and "positively affected".

Figure 5:
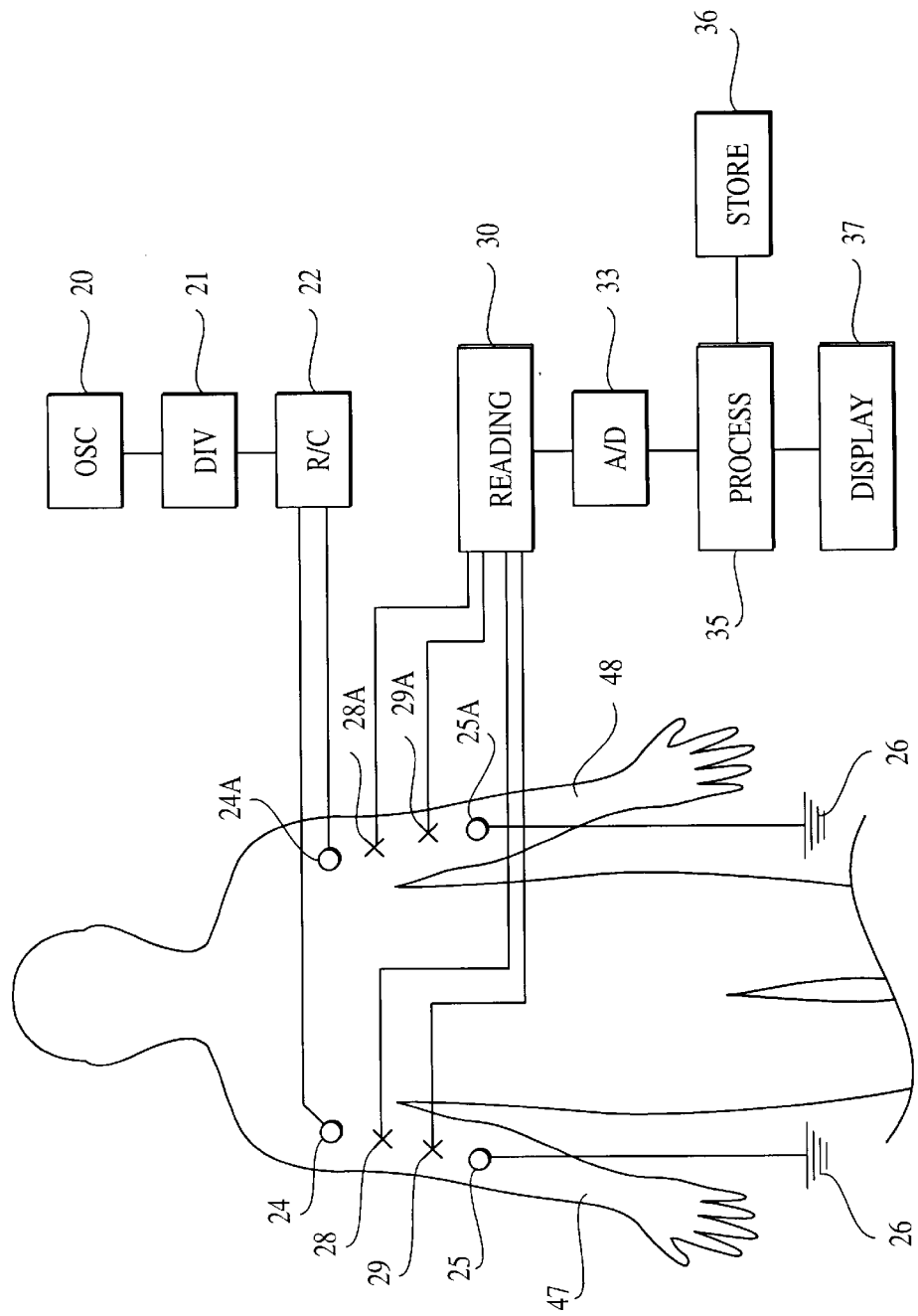
FIG. 5 is a diagram of the apparatus of the invention applied simultaneously to both arms of a subject.

As shown in FIG. 5, it is within the scope of the invention to include a two channel bioimpedance meter with duplication of peripheral accessories so that measurements of both sides of a subject can occur simultaneously. In this case, current is simultaneously passed between electrodes 24, 25 on one arm 47 and electrodes 24A, 25A on the opposite arm 48. Monitoring electrodes 28, 29 on the first arm 47 measure bioelectrical impedance while monitoring electrodes 28 A, 29 A measure bioelectrical impedance on the opposite arm 48. A measuring meter 30 has two channels for simultaneously monitoring signals provided from the monitoring electrodes 28, 29, 28A, 29A. The signals are passed through an analogue/digital converter 33 and then analysed by processor 35. The results are stored in storing unit 36 and shown on display 37.

Figure 6:
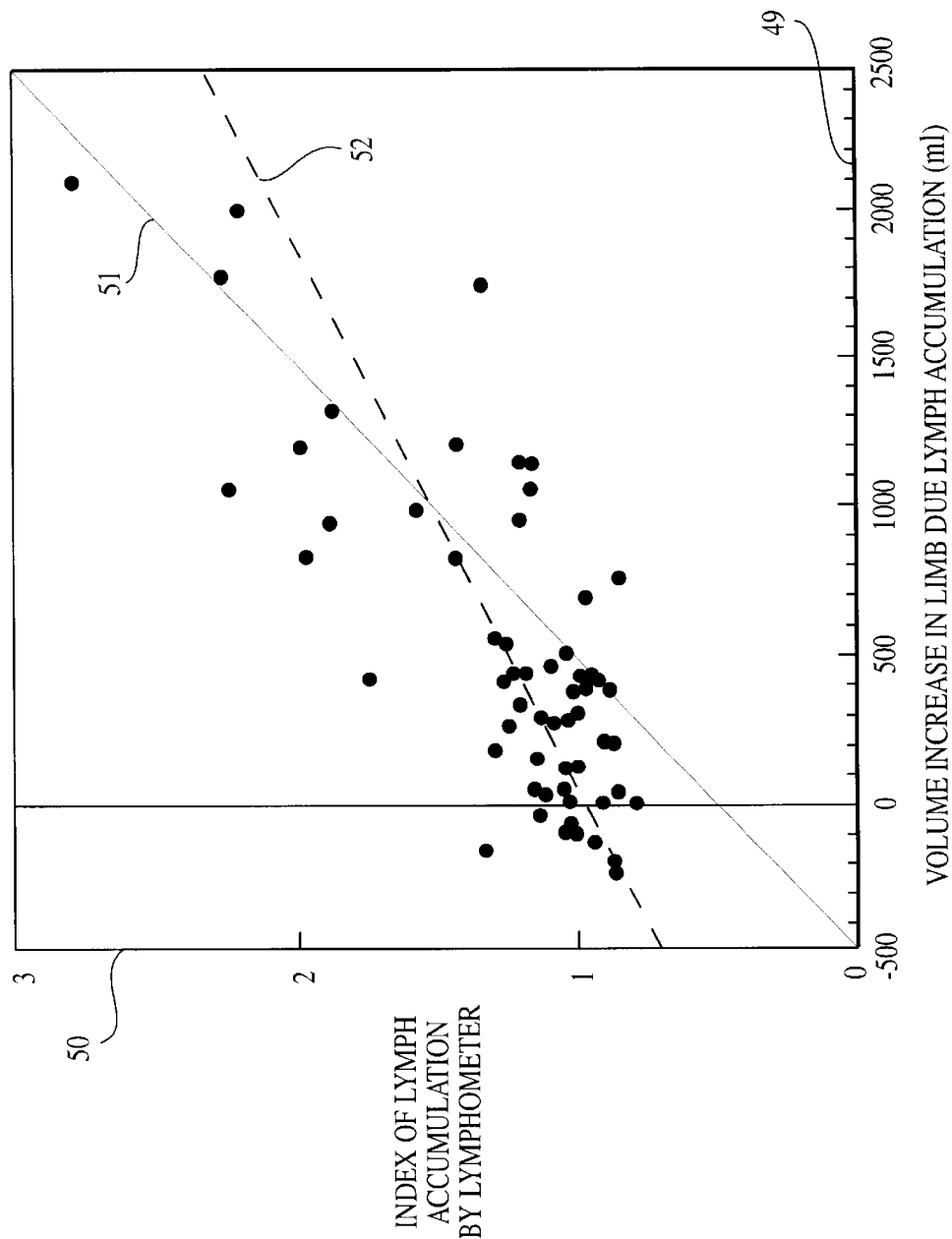
FIG. 6 represents the results of correlation analysis between circumferential changes in a limb and results from the apparatus of the invention.

FIG. 6 is correlation of results obtained from the present invention when compared to volume assessed from circumferential changes of a limb. The X axis 49 represents volume increase in a limb during a one year period. The Y axis 50 is an indicator of lymph accumulation as measured by the apparatus of the invention. The line 51 is the line of identity and the broken line 52 is the line of best fit. The correlation between the two methods is high at 0.75. Measurement of circumference is currently the most commonly used method of assessing lymphoedema.

The discussion has referred to both oedema and lymphoedema, as it is clear to a skilled addressee that the above method and apparatus may be utilised on any form of tissue oedema. However, it is also likely that the predominant use of the method and apparatus will be directed mainly to lymphoedema due to its clinical relevance. However, this may change in a specific situation or with time. The method may also be used in comparing a reading from one anatomical region with a separate unpaired region. For example, a reading taken on central localised oedema (eg. ascites) may be referenced against a nonoedematous structure such as a limb.

Throughout the specification, the aim has been to describe the preferred embodiments of the invention without limiting the invention to any one embodiment or specific collection of features. Various changes and modifications may be made to the embodiments described and illustrated without departing from the present invention.

The claims defining the invention are as follows:

1. A method of assessing tissue oedema comprising the steps of:
    performing a first measurement of bioelectrical impedance of a first anatomical region in a subject at a single low frequency alternating current;
    performing a second measurement of bioelectrical impedance of a second anatomical region in the same subject at the same low frequency alternating current; and
    analysing the first and second measurements to obtain an indication of the presence of tissue oedema;
    wherein the step of analysing the first and second measurements to obtain an indication of the presence of tissue oedema includes the step of applying the algorithm:

$$F = \frac{Z_h}{Z_l} - cf$$

where:
F is an indication of tissue oedema;
$Z_h$ is the greater bioelectrical impedance reading;
$Z_l$ is a lesser bioelectrical impedance reading; and
cf is a correcting factor.

2. The method of claim 1 wherein the correcting factor is 1.066.

3. The method of claim 1, wherein the first anatomical region and the second anatomical region are paired and wherein one of the anatomical regions is unaffected by tissue oedema.

4. The method of claim 1, wherein the first anatomical region and the second anatomical region are dissimilar and wherein one of the anatomical regions is unaffected by tissue oedema.

5. The method of claim 1, wherein the first anatomical region and the second anatomical region are the same and wherein the first measurement and the second measurement are separated in time.

6. The method of claim 1, wherein the anatomical regions are limbs or parts of limbs.

7. The method of claim 1, wherein the single low frequency alternating current is in the range of 5 to 20 kHz.

8. The method of claim 7, wherein the single low frequency alternating current is in the range of 10 to 15 kHz.

9. The method of claim 8, wherein the single low frequency alternating current is 10 kHz.

10. The method of claim 1, further including the step of establishing a correcting factor for analysing the two measurements.

11. The method of claim 10, wherein the step of establishing a correcting factor includes the step of obtaining bioelectric impedance measurements from a plurality of subjects unaffected by tissue oedema.

12. An apparatus for determining the presence of tissue oedema, including:
 current means for applying an alternating current to an anatomical region at a single frequency;
 monitoring means to monitor the bioelectrical impedance of said region and produce signals characteristic of bioimpedance; and
 analysis means to analyse the signals indicative of bioimpedance to provide an indication of tissue iedema;
 wherein the analysis means is programmed to analyse data according to the algorithm:

$$F = \frac{Z_h}{Z_l} - cf$$

where:
 F is an indication of the presence of tissue oedema;
 $Z_h$ is a greater bioelectrical impedance measurement;
 $Z_l$ is a lesser bioelectrical impedance measurement; and
 cf is the correcting factor.

13. The apparatus of claim 12, wherein the current means is a proximal electrode and a distal electrode in connection with a power source.

14. The apparatus of claim 12, the monitoring means is a first connection and a second connection for location on or near the anatomical region.

15. The apparatus of claim 12, wherein the analysis means is at least one processing means programmed to perform analysis of data to provide an indication of the presence of tissue oedema.

16. The apparatus of claim 12, further including means for recording bioimpedance in two anatomical regions of the same subject simultaneously.

17. A method of assessing tissue oedema comprising the steps of:
 performing a first measurement of bioelectrical impedance of a first anatomical region in a subject at a single low frequency alternating current;
 performing a second measurement of bioelectrical impedance of a second anatomical region in the same subject at the same low frequency alternating current; and
 analysing the first and second measurements to obtain an indication of the presence of tissue oedema;
 wherein the step of analysing the first and second measurements to obtain an indication of the presence of tissue oedema includes the step of applying the algorithm:

$$F = cf_1 - \frac{Z_l}{Z_h}$$

where:
 F is an indication of tissue oedema;
 $cf_1$ is a correcting factor;
 $Z_l$ is a lesser bioelectrical impedance reading, and
 $Z_h$ is a greater bioelectrical impedance reading.

18. The method of claim 17, when used on paired limbs and $cf_1=0.862$.

19. The method of claim 17, wherein the first anatomical region and the second anatomical region are paired and wherein one of the anatomical regions is unaffected by tissue oedema.

20. The method of claim 17, wherein the first anatomical region and the second anatomical region are dissimilar and wherein one of the anatomical regions is unaffected by tissue oedema.

21. The method of claim 17, wherein the first anatomical region and the second anatomical region are the same and wherein the first measurement and the second measurement are separated in time.

22. The method of claim 17, wherein the first and second anatomical regions are limbs or parts of limbs.

23. The method of claim 17, wherein the single low frequency alternating current is in the range of 5 to 20 kHz.

24. The method of claim 23, wherein the single low frequency alternating current is in the range of 10 to 15 kHz.

25. The method of claim 24, wherein the single low frequency alternating current is 10 kHz.

26. The method of claim 17, further including the step of establishing a correcting factor for analysing the two measurements.

27. The method of claim 26, wherein the step of establishing a correcting factor includes the step of obtaining bioelectrical impedance measurements from a plurality of subjects unaffected by tissue oedema.

28. An apparatus for determining the presence of tissue oedema, including:
 current means for applying an alternating current to an anatomical region at a single frequency;
 monitoring means to monitor the bioelectrical impedance of said region and produce signals characteristic of bioimpedance; and analysis means to analyse the signals indicative of bioimpedance to provide an indication of tissue oedema; wherein the analysis means is programmed to analyse data according to the algorithm:

$$F = cf_1 - \frac{Z_l}{Z_h}$$

where:
 F is an indication of tissue oedema;
 $cf_1$ is a correcting factor;
 $Z_l$ is a lesser bioelectrical impedance measurement; and
 $Z_h$ is a greater bioelectrical impedance measurement.

29. The apparatus of claim 28, wherein the current means is a proximal electrode and a distal electrode in electrical connection with a power source.

30. The apparatus of claim 28, wherein the monitoring means is a first connection and a second connection for location on or near the anatomical region.

31. The apparatus of claim 28, wherein the analysis means is at least one processing means programmed to perform analysis of data to provide an indication of the presence of tissue oedema.

32. The apparatus of claim 28, further including means for recording bioimpedance in two anatomical regions of the same subject simultaneously.

* * * * *